(12) United States Patent
Leek

(10) Patent No.: US 6,828,154 B1
(45) Date of Patent: Dec. 7, 2004

(54) STAINING METHOD WITH CHROMIC ACID PRECURSORS

(75) Inventor: Adrian Elmer Leek, Hingham, MA (US)

(73) Assignee: Cytologix Corporation, Cambridge, MA (US)

( * ) Notice: Subject to any disclaimer, the term of this patent is extended or adjusted under 35 U.S.C. 154(b) by 262 days.

(21) Appl. No.: 09/705,970

(22) Filed: Nov. 3, 2000

(51) Int. Cl.$^7$ .................. G01N 35/00; G01N 33/48
(52) U.S. Cl. ..................... 436/43; 436/46; 436/63
(58) Field of Search .................. 436/43, 46, 63, 436/144

(56) References Cited

U.S. PATENT DOCUMENTS

| | | | |
|---|---|---|---|
| 3,431,886 A | * | 3/1969 | McCormick et al. |
| 5,316,452 A | | 5/1994 | Bogen et al. |
| 5,322,771 A | | 6/1994 | Rybski et al. |
| 5,645,114 A | | 7/1997 | Bogen et al. |
| 5,695,942 A | | 12/1997 | Farmilo et al. |
| 6,092,695 A | | 7/2000 | Loeffler et al. |

FOREIGN PATENT DOCUMENTS

WO     WO 99/63342     12/1999

OTHER PUBLICATIONS

Roy (Stain Technology vol. 58, No. 4, pp 215–218), 1983.*
Morse, A., in "Theory and Practice of Histological Techniques," 4$^{th}$ Edition, Churchill Livingston, Ed. Bancroft, J.D., Stevens, A., Chapter 24, 525 (1996).

Histopathologic Methods and Color Atlas of Special Stains, by L. G. Luna, American Histolabs, Inc., Gaithersburg, MD, 200–202 (1992).

Anderson, G. and Scott, M., in "Determination of Product Shelf Life and Activation Energy for Five Drugs of Abuse," Clin. Chem. 37(3), 398–401 (1991).

"*Advanced Inorganic Chemistry 5$^{th}$ Edition*" F. Albert Cotton and Geoffrey Wilksinson, eds. (NY:John Wiley & Sons), pp 679–695(1981).

Lee G. Luna, "*Stability of Commonly Used Staining Solutions*", at www.histology.to/shelf_lifefaq.html.

\* cited by examiner

*Primary Examiner*—Mark Navarro
(74) *Attorney, Agent, or Firm*—Hamilton, Brook, Smith & Reynolds, P.C.

(57) ABSTRACT

A method of staining a biological specimen in an automated staining protocol includes contacting the biological specimen with two or more precursors of a staining reagent. When combined, the precursors form the staining reagent or have the same effects on the biological specimen as the staining reagent. Preferably, the precursors are more compatible with the liquid dispensers employed in their delivery than is the staining reagent. In one example, a GMS protocol employs, instead of chromic acid, a combination of perchloric acid and sodium chromate.

4 Claims, No Drawings

STAINING METHOD WITH CHROMIC ACID PRECURSORS

BACKGROUND OF THE INVENTION

Increasingly, histological examination of biological specimens is being performed under automated conditions. Equipment and protocols have been developed for many automated routine stains and there is increased interest in automating non-routine, complex or special stains.

During manual staining, staining reagents can be safely prepared and stored according to conventional laboratory procedures. Corrosive reagents required in some staining protocols, for example, are stored according to safety guidelines, often in glass containers, and are dispensed as needed during the staining procedure.

In automated staining systems, however, reagent packs, valve parts, and other instrument components often are constructed from plastic materials, for example from clear and flexible elastomeric polymers. Such materials are incompatible with some of the chemical reagents required in staining protocols and the problem is exacerbated when the staining reagent is stored at room temperature and/or for prolonged periods of time. Storing staining reagents in liquid dispensers fabricated from plastic materials with which they are incompatible can result in leaks, loss of liquid, loss of accurate dispensing, as well as ii safety hazards.

Therefore, a need exists for automated staining procedures which eliminate or minimize the aforementioned problems.

SUMMARY OF THE INVENTION

The methods of the present invention are directed to staining processes. In particular, the methods described herein are related to combining precursors of a staining reagent and contacting the combined precursors with a biological specimen. The methods of the invention can be carried out in an automated staining process which uses liquid dispensers to dispense staining reagents. In one embodiment of the invention, the staining protocol requires the use of a staining reagent which is incompatible with at least one material, (e.g., plastic) employed in the fabrication of the liquid dispenser. One example of a staining reagent is chromic acid which is used in Grocott's Modification of Gomori's Methenamine Silver (GMS) stain which is typically employed to detect fungi in cytological or histological specimens.

In one embodiment, the method of the invention includes providing a biological specimen, for instance on a microscope slide, and dispensing onto the biological specimen two or more precursors of the staining reagent. The precursors are delivered from separate liquid dispensers. When combined, such as, for example by contacting one another on the biological specimen, the precursors either form the staining reagent in situ or have the same effect on the biological specimen as that of the staining reagent. Preferably, the precursors are more compatible with the liquid dispensers than is the staining reagent. In the case of chromic acid, an oxidizing precursor, such as, for instance, a source of chromate ions, and a source of hydrogen ions can be dispensed separately onto the biological specimen. The chromate ions and hydrogen ions form in situ chromic acid or, alternatively, have the same effect on the biological specimen as that of chromic acid, and the stain process proceeds according to the standard protocol.

In alternative embodiments, precursors of chromic acid also can be employed in staining procedures-which are carried out manually.

The invention has many advantages. For example, special stains requiring strong oxidizing agents or other corrosive staining reagents can be automated without changing the design or materials employed to fabricate the liquid dispensers. The precursors employed can be pre-packed and stored for longer periods or at higher temperatures than previously possible with the staining reagent itself. Safety hazards, leaks and inconsistent delivery of reagent amounts are minimized.

DETAILED DESCRIPTION OF THE INVENTION

The invention is related to staining biological specimens. Examples of biological specimens include, but are not limited to, tissue sections, cell cultures, smears, control samples, cell suspensions, cytospin preparations and others. In one embodiment of the invention, the biological specimen includes a tissue section suitable for histological staining.

Numerous staining procedures, also referred to herein as staining protocols, staining processes or staining methods, have been developed to visualize cell or tissue abnormalities and to detect, identify or characterize microorganisms present in a biological specimen. During staining protocols a biological specimen is contacted with staining reagents. The sequence and amounts in which the staining reagents are added to the biological specimen depend on the particular staining procedure, as known in the art. Special stains generally include numerous steps and often are some of the most complex tests performed in the laboratory. Numerous special stains have been developed for the histological analysis of tissue samples. For example, special stains exist for detecting the presence of microorganisms as would be associated with pathogen invasion, colonization or contamination of a biological specimen, such as a tissue sample. Such stains are referred to herein as histological stains.

In a preferred embodiment of the invention the staining procedure is suited to detect microorganisms or pathogens, in particular fungi. Fungi are described, for example, in Stevens. A., and Francis, R. J., in "Theory and Practice of Histological Techniques," $4^{th}$ Edition, Churchill Livingston, Ed. Bancroft, J. D. & Stevens, A., Chapter 14, 291–308 (1996). Specific examples of fungi include but are not limited to *Pneumocystis carinii, Aspergillus fumigatus, A. niger, Candida albicans, Crypococcus neoformans, Histoplasma capsulatum, Mucor* spp., *Nocardia asteroides* and *Rhizopus* spp. The methods of the invention also are suited to detect other pathogens such as, for instance, mycobacteria spp. and Schistosoma spp.

One example of a stain employed to detect fingi is Grocott's Modification of Gomori's Methenamine Silver method, also referred to herein as the Grocott's Methenamine Silver or the GMS method. Generally, GMS protocols include oxidizing alcohol (—OH) groups in cell-wall polysaccharides to aldehyde groups. In turn, aldehydes reduce methenamine silver nitrate to metallic silver. GMS stains typically highlight a fungus cell wall, causing it to be colored brown to black against a pale green background. The pale green is produced by brief counter-staining with Light Green dye.

Another example of a stain employed to detect fungi is Gridley's stain. Generally, Gridley's stain protocols involve oxidation of adjacent hydroxyl groups of cell wall polysaccharides to aldehyde groups. Aldehyde groups then react with Schiff's reagent, producing a reddish color. Typically, the stain causes cell walls to be purple to magenta and yeast to be rose to purple, with a yellow background.

Generally, the presence or absence of fungus is detected by staining the biological specimen and then examining the specimen under the microscope. If microorganisms are present, they can be distinguished by their color and shape. Generally, the examination is performed by a pathologist.

The invention is particularly related to automated staining procedures and can be employed in a number of automated staining protocols and in conjunction with instruments, controls and software known in the art. In a preferred embodiment, the staining procedure is an automated staining procedure employed to detect, identify or characterize fungi and bacteria. The skilled practitioner also can employ the present invention, without undue experimentation, in conjunction with new automated staining procedures, new instrumentation, control systems and software as such are being developed.

During automated procedures the biological specimen is affixed, smeared, attached, supported or otherwise provided, generally on a planar platform, such as a microscope slide. More than one specimen can be provided on a single slide. Commonly, the slide is a glass slide but slides made out of other materials that are compatible with the biological specimen and staining reagents can also be used. Optionally, the slides can be separated from one another by dividing walls, thereby preventing reagent spills from one slide to another.

The Artisan™ slide staining system, sold by CytoLogix Corporation, is a particularly preferred configuration for using this invention. In this configuration, a slide bearing a thin biologic specimen, such as a tissue section or cells, is positioned on a rotary carousel. The carousel's positioning is specified under computer control, according to a pre-set program specified by the operator of the instrument. A second rotary carousel for carrying reagents (in liquid dispensers) is located above the carousel for holding slides. The positioning of the second carousel is also under computer control. To dispense a desired reagent onto a specific microscope slide, the two carousels are rotated so that a dispenser holding a reagent (mounted on the upper carousel) is positioned above a desired slide. An actuator causes the dispenser to dispense reagent onto the slide. The amount and sequence of reagent applications to slides are specified by the particular staining protocol. The protocols often include washing steps, to remove reagent after the reaction has completed. The protocols also provide for the collection of spent reagent into selected containers. Automated staining procedures generally are controlled by control systems integrated with computer software, as known in the art.

Suitable liquid dispensers which can be employed in automated staining are described, for instance, in U.S. Pat. Nos. 5,645,114 and 5,316,452 to Steven A. Bogen, et al.; the entire contents of both are incorporated herein by reference. A preferred liquid dispenser design is described in U.S. Pat. No. 6,092,695 to Herbert H. Loeffler, the entire contents of which are incorporated herein by reference. The term "liquid dispenser" is used herein interchangeably with "reagent pack".

Liquid dispensers generally include a reservoir, a metering chamber and at least one valve. In whole or in part, liquid dispensers are fabricated from plastic materials. Flexible plastic materials are preferred. Clear, i.e, translucent or transparent, materials are advantageous as they allow viewing of the staining reagent. For example, the formation or presence of gas bubbles in the liquid staining reagent can be detected and the bubbles can be evacuated to ensure consistent delivery of the same liquid volume to each sample being stained.

Examples of plastic materials which are flexible and also clear include, but are not limited to elastomers such as silicone elastomers or silicone rubber, also referred to herein as silicone, ethylene-propylene terpolymers, often abbreviated as EPT, and in particular terpolymers made from ethylene propylene diene monomer, also referred to herein as EPDM. Liquid dispensers can be fabricated from a single plastic, also referred to herein as polymeric, material or can include parts fabricated from different plastic or polymeric materials. In a preferred embodiment of the invention, the liquid dispensers are fabricated from silicone.

Plastic materials, however, are incompatible with some corrosive chemical reagents, which, as known in the art, are commonly stored in glass containers or other non-plastic ware. When in contact with plastics such reagents can cause changes of color, wear and erosion of the plastic material. These changes tend to take place more rapidly at higher temperatures and can be slowed by lowering the temperature. Sources that list chemical reagents and rate their compatibility with various plastic materials are generally known in the art and often can be obtained from manufacturers of plastic ware. Frequently, laboratory procedures also identify reagents that cannot be safely stored in plastic containers.

The present invention is related to staining protocols which include using a corrosive reagent, such as the reagents described above. The methods of the invention relate to separately providing precursor compounds which are less-corrosive, and, in some cases, more stable than a corrosive reagent itself. The precursors are stored separately and are combined in the course of the staining procedure. For example, the precursors can be combined substantially immediately before contacting the biological specimen being stained or preferably, as they contact the biological specimen.

In a preferred embodiment of the invention, two or more precursors of the staining reagent are separately dispensed onto the biological specimen or onto the slide where they combine or react. Precursors can wet the entire specimen or can be delivered to a localized spot thereupon.

In a further embodiment, the precursors are first combined and the resulting mixture contacts the biological specimen. For example, the precursors can be combined in a container such as a test tube and the resulting mixture can be dispensed onto the biological specimen. In one embodiment of the invention, the precursors are combined and the resulting mixture contacts the biological specimen in an automated staining instrument.

Once the precursors are combined, they produce the same effect on the biological specimen as that of the staining reagent. Preferably, upon being combined, the precursors form in situ staining reagent.

Generally, precursors are delivered in amounts selected to result in a desired concentration of the staining reagent. Precursor amounts can be optimized to form the staining reagent or to have the same effect on the biological specimen as the staining reagent itself In one embodiment of the invention, the precursors can be added in any sequence. Alternatively, specific sequences of adding the precursors can be employed. Conditions such as solvent systems, pH, temperature and others can be selected based on the particular reaction(s) chemistry, as known in the art.

In a preferred embodiment, the combination of precursors dispensed onto the biogical specimen render the biological specimen suitable for subsequent staining. For example, the combination precursor reagents are washed away, as known in the art, and the washed specimen is the subjected to the remaining steps of the staining protocol, including staining it with a suitable histological stain. After a specified step of a protocol is completed, the waste solutions can be collected and disposed of, as known Preferably, the precursors are more compatible with the liquid dispenser, i.e., the plastic material(s) employed to fabricate the liquid dispenser, than is the staining reagent. For example, in comparison to the staining reagent itself, each of the precursors can be stored in the liquid dispenser for a longer period of time, at a given temperature, before causing damage to the plastic material(s). In one embodiment of the invention, the precursors can be stored in the liquid dispensers, at room temperature, for a period of at least 240 days without causing any detectable damage to the plastic materials employed to fabricate any of the liquid dispenser parts. Alternatively, the precursors can be stored for a given time period at a higher temperature, without causing damage to the plastic material(s), than is possible in the case of the staining reagent itself.

One example of a staining reagent which is incompatible with plastic materials typically employed in the fabrication of liquid dispensers, such as silicone rubber or EPDM, is chromic acid. As used herein, chromic acid refers to a solution of chromium trioxide, also known as chromic anhydride or $CrO_3$.

Chromic acid is used, for instance, in GMS and Gridley's stain protocols for staining fungi such as Pneumocystis carinii, Aspergillus spp., Histoplasma capsulatum and others in histological or cytological samples. Suitable protocols for GMS and Gridley's stains are described in Histopathologic Methods and Color Atlas of Special Stains, by L. G. Luna, American Histolabs, Inc., Publications Division, (1992). In these stains, chromic acid is thought to act as the oxidizing agent which converts alcohol groups present in the polysaccharide cell-wall to aldehyde groups and renders them susceptible to stain.

In a preferred embodiment of the invention, a stain protocol which typically requires chromic acid is modified to employ precursors which, when combined, either form chromic acid or have the same effect, when in contact with the biological specimen, as that of chromic acid. In one embodiment, the precursors include an oxidizer, for example a source of chromate ions $(CrO_4)^{2-}$, and a source of hydrogen ions (H+). Suitable sources of chromate ions are compounds other than chromic acid and include chromate salts, such as, for instance, sodium chromate, potassium chromate, ammonium chromate, dichromates, such as, for instance, sodium or potassium dichromate. Sodium chromate is preferred. Suitable sources of hydrogen ions are acids other than chromic acid and include perhalogenated acids such as perchloric or perbromic acids. Other sources of hydrogen ions include nitric acid, $HNO_3$. Perchloric acid ($HClO_4$) is preferred. By using the two precursors, the acid properties and oxidizing properties of chromic acid are separately provided.

Without wishing to be bound by any mechanism in interpreting the invention, it is believed that between pH 2 and pH 6, $(HCrO4)^-$ and $(Cr_2O_7)^+$ are in equilibrium, while at lower pH values, i.e., less than pH 1, the main species found is $H_2CrO_4$. For hydrogen ions provided via nitric or perchloric acids, the equilibria are as shown bellow:

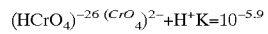

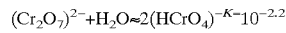

For example, in the GMS stain protocol, a 5% chromic acid solution is used to treat a biological specimen on a microscopic slide and render it suitable for staining with a silver compound. As described herein, a solution of 10% perchloric acid and a solution of 10% sodium chromate are separately dispensed in equal parts directly onto a biological specimen. The combination has the equivalent effect on the biological specimen as that of 5% chromic acid.

It is extremely advantageous to be able to use precursors instead of chromic acid in an automated staining procedure. As described herein, chromic acid precursors, perchloric acid and sodium chromate, are less corrosive to plastic reagent packs and valves that are typically used in automated staining protocols. In particular, these two precursors are significantly less corrosive towards liquid dispensers fabricated from silicone and can be safely stored in silicone reagent packs for at least three months.

In alternative embodiments, chromic acid precursors also can be used in manual staining protocols.

The invention is further described through the following examples which are provided for illustrative purposes and is not intended to be limiting.

EXAMPLES

Example 1

GMS Stain Using Chromic Acid

A protocol which includes chromic acid and is suitable for an automated GMS stain, which was developed for the Artisan Staining System provided by CytoLogix™ Corporation, Cambridge, Mass., has the following six steps with a sequence of rinses between each:

1. Add 1 mL 5% chromic acid to the slide, mix 3 times, and heat to 45° for 570 (630) seconds. Remove the chromic acid, and rinse 4 times with 3 mL each of Wash Solution.
2. Add 1 mL sodium bisulfite solution to the slide, mix twice, and incubate without heating for 570 (630) seconds. Remove the bisulfite, and rinse 4 times with 3 mL each of Wash Solution.
3. Add 1 mL 0.21% silver nitrate solution and 1 mL of 3% Methenamine in borate buffer to the slide, mix 3 times, and heat to 62° for 570 (630) seconds. Add 1 mL Wash Solution to the silver/Methenamine mixture, mix twice, remove all the liquid, and rinse 3 times with 3 mL each of Wash Solution.
4. Add 1 mL gold chloride solution to the slide, mix once, and incubate without heating for 570 (630) seconds. Remove the liquid, and rinse 3 times with 2 mL each of Wash Solution.
5. Add 1 mL 2% sodium thiosulfate solution to the slide, mix twice, and incubate without heating for 570 (630) seconds. Remove the liquid, and rinse 3 times with 2 mL each of Wash Solution.
6. Add 1 mL Light Green dye solution to the slide, mix twice and immediately remove the liquid. Rinse twice with 3 mL each of Wash Solution, then twice with 3 mL each of 95% ethanol and finally twice with 3 mL each of absolute ethanol.

One protocol version uses incubations of 570 seconds which is sufficient to detect most fungi of histological interest. Another protocol version uses the longer incubation (630 seconds) to detect *Pneumocystis carinii*. In this variant, the incubation temperature in step 3 is slightly lower –60° C.).

Example 2

GMS Stain Using Chromic Acid Precursors

Step 1 of the protocol is changed as follows. Instead of adding 1 mL of 5% chromic acid, 1 mL of 10% sodium chromate and 1 mL of 10% perchloric acid are added. This results in 2 mL of liquid containing these concentrations of the hydrogen ($H^+$) and chromate ($CrO_{4-}$) ions as does the 1 mL of 5% chromic acid, and the end result in terms of staining the target organisms is identical.

The staining protocol then proceeds as follows:

2. Add 1 mL sodium bisulfite solution to the slide, mix twice, and incubate without heating for 570 (630) seconds. Remove the bisulfite, and rinse 4 times with 3 mL each of Wash Solution.
3. Add 1 mL 0.21% silver nitrate solution and 1 mL of 3% Methenamine in borate buffer to the slide, mix 3 times, and heat to 62° for 570 (630) seconds. Add 1 mL Wash Solution to the silver/Methenamine mixture, mix twice, remove all the liquid, and rinse 3 times with 3 mL each of Wash Solution.
4. Add 1 mL gold chloride solution to the slide, mix once, and incubate without heating for 570 (630) seconds. Remove the liquid, and rinse 3 times with 2 mL each of Wash Solution.
5. Add 1 mL 2% sodium thiosulfate solution to the slide, mix twice, and incubate without heating for 570 (630) seconds. Remove the liquid, and rinse 3 times with 2 mL each of Wash Solution.
6. Add 1 mL Light Green dye solution to the slide, mix twice and immediately remove the liquid. Rinse twice with 3 mL each of Wash Solution, then twice with 3 mL each of 95% ethanol and finally twice with 3 mL each of absolute ethanol.

Example 3

Comparison of Corrosiveness of Chromic Acid and Chromic Acid Precursors

The effects of $H_2CrO_4$ on liquid dispenser parts employed in the Artisan™ Staining System were compared with those of the chromic acid precursors, sodium chromate and perchloric acid. The two plastic materials employed in the liquid dispenser parts were GE Bayer 2070 silicone rubber, and Royalene$^R$ EPDM 501 obtained from Uniroyal Chemical. The experiments evaluated the functional integrity of the dispenser tip and non-return valve (the parts fabricated of silicone or EPDM). Dispensing or squirt capabilities also were studied.

The effects (functional integrity of the dispenser tip and non-return valve) of chromic acid were studied at 45° C. (Tables 2 and 3). Equivalent effects at lower temperatures may be reasonably expected to be as shown in Table 1. Table 1 is based on an extrapolation of the Arrhenius Equation for the calculation of reagent stability (Anderson, Geoffrey and Milda Scott. 1991. Determination of product shelf life and activation energy for five drugs of abuse, Clinical Chemistry 37(3):398–401). Table 1 lists three columns, each representing product storage at the specified temperature. Equivalent stability, or in this case material degradation from chromic acid, might theoretically be expected for each of the times indicated in each row. For example, the top row indicates that the amount of material degradation that occurs in 7 weeks at 4° C. would only require 3 days at 45° C. or 15 days at 20° C.

TABLE 1

| Time at 45° C. | Time at 4° C. | Time at 20° C. |
|---|---|---|
| 3 days | 7 weeks | 15 days |
| 7 days | 4 months | 1 month |
| 15 days | 8 months | 2½ months |
| 21 days | 11 months | 3½ months |
| 28 days | 15 months | 4½ months |
| 38 day | 1½ years | 6 months |
| 51 days | 2¼ years | 9 months |

The effects of 5% chromic acid at 45° C. on the parts and operation of two liquid dispensers are shown in Tables 2 and 3. That the tip is leaking indicates that its functionality has been compromised by the reagent. The functionality of the valve is indicated by the ability of the tip to squirt (when compressed). The ratio in the column headed with the word "squirt" indicates the number of dispenser tips (out of a total of 3) that dispensed liquid after the indicated time of storage.

TABLE 2

5% chromic acid with silicone rubber valves and tips (n = 3)

| time at 45° | tip | squirt |
|---|---|---|
| 1 day | OK | 3/3 |
| 15 days | no leak discolored | 1/3 |
| 18 days | no leak discolored | 1/3 |
| 19 days | no leak discolored | 0/3 |

TABLE 3

5% chromic acid with EPDM valves and tips (n = 3)

| time at 45° | tip | squirt |
|---|---|---|
| 1 day | discolored | 3/3 |
| 15 days | 3/3 leaking | 3/3 |
| 18 days | 3/3 leaking | 3/3 |

The effects of 10% perchloric acid on silicone and EPDM liquid dispensers is shown in Tables 4 and 5, respectively.

TABLE 4

10% perchloric acid with silicone rubber valves and tips (n = 3)

| time at 45° | tip | squirt |
|---|---|---|
| 7 days | OK | 3/3 |
| 14 days | OK | 3/3 |
| 21 days | OK | 3/3 |
| 28 days | 1/3 OK 2/3 slight leak | 3/3 |
| 38 days | 3/3 slight leak | 3/3 |
| 51 days | 3/3 slight leak | 3/3 |
| 59 days | 3/3 dripping | 1/3 |

TABLE 5

10% perchloric acid with EPDM
valves and tips (n = 5)

| time at 45° | tip | squirt |
|---|---|---|
| 7 days | OK | 5/5 |
| 14 days | 5/5 partly discolored, 5/5 slight leak | 5/5 |
| 21 days | 5/5 partly discolored, 3/5 slight leak | 5/5 |
| 28 days | 4/5 dripping | 5/5 |
| 38 days | all discolored all dripping | 5/5 |

The effects of 10% sodium chromate on the silicone and EPDM liquid dispensers are shown in Table 6 and 7, respectively.

TABLE 6

10% sodium chromate with silicone rubber
valves and tips (n = 3)

| time at 45° | tip | squirt |
|---|---|---|
| 7 days | OK no leaks | 3/3 |
| 14 days | OK no leaks | 3/3 |
| 21 days | OK no leaks | 3/3 |
| 28 days | OK no leaks | 3/3 |
| 38 days | OK no leaks | 3/3 |
| 51 days | OK no leaks | 3/3 |

TABLE 7

10% sodium chromate with EPDM
valves and tips (n = 5)

| time at 45° | tip | squirt |
|---|---|---|
| 7 days | OK | 5/5 |
| 14 days | OK | 5/5 |
| 21 days | OK | 5/5 |
| 28 days | OK | 5/5 |
| 38 days | 1/5 slight leak | 5/5 |
| 51 days | 4/5 dripped after squirting | 5/5 |

The "slight leak" in Tables 4, 5, and 7 was a droplet formed on the extremity of the tip. As no liquid was seen to have fallen from the tip, it is assumed that this resulted from differential thermal expansion of the liquid and the tip expelling a small amount of liquid. The phrase "slight leak" therefore does not represent failure of the plastic component.

The results indicated that the functional integrity of the dispenser (flexible parts fabricated of either silicone or EPDM) is compromised by contact with chromic acid (5%) for 15 days at 45° C. By contrast, the functional integrity of the flexible parts fabricated of silicone was essentially maintained after contact with either 10% perchloric acid or 10% sodium chromate for at least 51 days at 45° C. The functional integrity of the flexible parts fabricated of EPDM was compromised after 28 days in contact with 10% perchloric acid at 45° C.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of staining a biological specimen with a histological stain, wherein the specimen is treated by a process that includes treatment with a corrosive reagent, the process comprising the steps of:
   (a) dispensing onto a biological specimen an oxidizer that is a precursor of the corrosive reagent; and
   (b) dispensing onto the biological specimen an acid source of hydrogen ions that is other than the corrosive reagent, wherein the acid source of hydrogen ions is selected from the group consisting of perchloric acid, perbromic acid and nitric acid,
whereby the oxidizer combines with hydrogen ions and the combination of oxidizer and hydrogen ions contacts the biological specimen, thereby treating the biological specimen with the corrosive reagent.

2. The method of claim 1 wherein the acid source of hydrogen ions is perchloric acid.

3. A method for detecting the presence or absence of microorganisms in a biological specimen in an automated histological staining process, comprising the steps of:
   (a) treating the biological specimen with a staining reagent wherein the treatment comprises dispensing from separate liquid dispensers, onto the biological specimen, a source of chromate ions and an acid source of hydrogen ions, the source of chromate ions and the acid source of hydrogen ions being other than chromic acid, wherein the acid source of hydrogen ions is selected from the group consisting of perchloric acid, perbromic acid and nitric acid, thereby combining chromate ions and hydrogen ions, wherein the combination of chromate ions and hydrogen ions contacts the biological specimen;
   (b) washing the combination of chromate ions and hydrogen ions from the specimen;
   (c) staining the washer specimen with a histological stain suitable for the detection of microorganisms; and,
   (d) detecting the presence or absence of microorganisms in the specimen.

4. The method of claim 3 wherein the acid source of hydrogen ions is perchloric acid.

* * * * *

UNITED STATES PATENT AND TRADEMARK OFFICE
CERTIFICATE OF CORRECTION

PATENT NO. : 6,828,154 B1  Page 1 of 1
DATED : December 7, 2004
INVENTOR(S) : Adrian Elmer Leek It is certified that error appears in the above-identified patent and that said Letters Patent is hereby corrected as shown below:

Column 10,
Line 53, delete the word "washer" and replace with the word -- washed --

Signed and Sealed this

Eighth Day of March, 2005

JON W. DUDAS
*Director of the United States Patent and Trademark Office*